US00PP36744P3

(12) United States Plant Patent
Gmitter, Jr.

(10) Patent No.: US PP36,744 P3
(45) Date of Patent: Jun. 17, 2025

(54) MANDARIN PLANT NAMED 'RES 19-56'

(50) Latin Name: ***Citrus reticulata* hybrid**
Varietal Denomination: RES 19-56

(71) Applicant: Florida Foundation Seed Producers, Inc., Marianna, FL (US)

(72) Inventor: Frederick Gmitter, Jr., Lakeland, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 18/751,578

(22) Filed: Jun. 24, 2024

(65) Prior Publication Data

US 2025/0008854 P1 Jan. 2, 2025

Related U.S. Application Data

(60) Provisional application No. 63/510,556, filed on Jun. 27, 2023.

(51) Int. Cl.
*A01H 5/08* (2018.01)
*A01H 6/78* (2018.01)

(52) U.S. Cl.
USPC ..... Plt./202
CPC ..... *A01H 6/785* (2018.05)

(58) Field of Classification Search
USPC ..... Plt./202
CPC ..... A01H 6/785; A01H 5/08
See application file for complete search history.

(56) References Cited

U.S. PATENT DOCUMENTS

PP31,347 P2 1/2020 Gmitter, Jr.

*Primary Examiner* — Keith O. Robinson
(74) *Attorney, Agent, or Firm* — Koenig IP Works, PLLC; Katherine Koenig

(57) ABSTRACT

A new and distinct seedless, easy to peel mandarin hybrid, named 'RES 19-56', with a unique clustered fruit bearing habit that can appeal to citrus hobbyists as an ornamental, but that also has shown potential value for premium early season fresh market production by CUPS or other *Citrus* growers. Has shown the ability to set large numbers of parthenocarpic fruit in the CUPS production system. These clusters sometimes number 15 or more fruit, having many more than fruit per cluster than other seedless mandarin hybrids.

16 Drawing Sheets

Genus and species: *Citrus reticulata* hybrid.
Cultivar denomination: 'RES 19-56'.

CROSS-REFERENCE TO RELATED APPLICATIONS

This Application claims the benefit of U.S. Provisional Patent Application No. 63/510,556, filed Jun. 27, 2023, which is incorporate by reference herein in its entirety.

ACKNOWLEDGEMENT OF FEDERAL RESEARCH SUPPORT

N/A.

BACKGROUND OF THE NEW CULTIVAR

The present invention relates to a new and distinct cultivar of *Citrus* (mandarin), botanically known as *Citrus reticulata* and hereinafter referred to by the name 'RES 19-56'.

The new mandarin cultivar 'RES 19-56' arose from a cross of 'Daisy' mandarin hybrid (not patented) x 'Mukaku Kishu' (also known as 'Seedless Kishu' mandarin; not patented), both publicly available and unprotected cultivars. The cross was made in 2005 in the experimental orchard in Gainesville, Florida. Seeds from the cross were planted in the greenhouse, and then following germination and seedling growth, a bud was grafted to 'Carrizo' citrange rootstock (not patented). The young, grafted tree was then grown off as a single stem plant with no branching. The tree was planted with many other hybrids with 0.3 m distance between each in the row. They were continuously trained to a single stem by repeated removal of all side sprouts as they appeared, and supported by a wire trellis until they reached approximately 4 m in height. At that time, the tops were bent over to induce spring flowering and fruit set. The new cultivar 'RES 19-56' was selected in 2010 and again in 2011 and submitted for cleanup, indexing, and certification by the State of Florida in 2014. Upon certification in 2016, several trees were propagated and planted in the field in April 2017 in Pasco County, FL. Fruit were first observed on these trees in 2019 and were found to be true to type. Additional trees were propagated and planted into a commercial *Citrus* under protective screen (CUPS) structure in 2019, and first crops were observed in 2021, which also produced true-to-type fruit.

Plant Breeder's Rights for this cultivar have not been applied for. The new *Citrus* (mandarin) cultivar 'RES 19-56' has not been made publicly available more than one year prior to the priority filing date of this application.

SUMMARY OF THE INVENTION

The new mandarin cultivar 'RES 19-56' has not been observed under all possible environmental conditions. The phenotype of the new cultivar may vary with variations in environment and cultural practices such as temperature, light intensity, fertilization, irrigation, and application of plant growth regulators without any change in genotype.

Trees of the new cultivar 'RES 19-56' are compact and bear fruit precociously, beginning in the second year after planting. This cultivar has a unique ability to set clusters of fruit that sometimes number as many as 15 fruit, or more. The fruit are completely seedless, very easy to peel, color well in the early season (September-November), and have good flavor. Individual fruit tend to have a neck at the stem end. It appears that they can set parthenocarpic fruit in the CUPS production system. By contrast, some other seedless hybrids in CUPS trials have not set many fruits, despite flowering normally.

Juice quality measurements for the new cultivar 'RES 19-56' were taken in an early harvest of 15 Sep. 2021: Brix was 9.9 and acidity was 0.6, for a ratio of 16.5, which is indicative of the very early maturity with good fruit quality. It was reported that fruit harvested at that time were green but developed good color following ethylene treatment and held up well in storage with no decay.

The trees grown in the field in Pasco County, Florida have held up well against *Citrus* huanglongbing or greening (HLB). Production has been good, with trees also exhibiting precocity and the fruit clustering phenotype as well. Experiments in CUPS systems have been closely monitored, and good potential for the fresh market production of early maturing mandarin fruit by 'RES 19-56' has been seen. To date, no major disease problems have been noted, although no rigorous, controlled testing for tolerance of diseases or pests has been conducted.

While the fresh *Citrus* market may be an important destination of fruit from 'RES 19-56', the unique and attractive appearance of the trees and particularly the many large clusters of brightly colored and parthenocarpic fruit provide another interesting possibility for commercialization. With its compact tree structure and obvious ornamental value, this cultivar could be an important addition to the inventories of nurseries who cater to this market.

The new cultivar 'RES 19-56' can be compared to the seed parent, 'Daisy', and the pollen parent, 'Mukaku Kishu'. All three cultivars share similar vegetative characteristics, although trees of 'RES 19-56' tend to be a bit smaller than either 'Daisy' or 'Mukaku Kishu'. The most obvious points of distinction are the fruit characteristics, but the resemblance of 'RES 19-56' to 'Mukaku Kishu' is greater than to 'Daisy'. Fruit of 'Daisy' are the larger of the three, fruit of 'Mukaku Kishu' are clearly the smallest, and fruit of 'RES 19-56' are of intermediate size between those of the parents. Fruit of 'Daisy' are oblate with a smooth surface texture, and are conspicuously seeded, especially with cross pollination. The dark orange peel is moderately adherent with conspicuous oil glands. In central Florida, fruit of 'Daisy' mature in November-December and can be borne in clusters of a few fruit. Fruit of 'Mukaku Kishu' are somewhat oblate but with a more conspicuous depression at the blossom end, and have a small neck at the stem end. The orange peel is slightly adherent so they are easy to peel, its texture is rugose, but oil glands are inconspicuous. Few clusters of fruit are seen generally, and they are completely seedless even with cross pollination. In central Florida, fruit of 'Mukaku Kishu' mature in late October into November. In contrast, fruit of 'RES 19-56' are also completely seedless even with abundant cross pollination, and they are more rounded than oblate in shape, with a less conspicuous depression at the blossom end, but have a similar small neck at the stem end. The peel texture of fruit of 'RES 19-56' is medium smooth, and internal and external colors are intermediate to the parents 'Daisy' and 'Mukaku Kishu' in central Florida conditions. Further, there is a strong tendency for fruit of 'RES 19-56' to be borne in multi-fruited clusters. They mature earlier than either parent, reaching commercial harvest usually by late September, and they will hold on the tree longer than fruit of 'Mukaku Kishu'. To summarize, fruit of 'RES 19-56' mature earlier and are larger in size than fruit of 'Mukaku Kishu', and they also mature earlier than fruit of 'Daisy', which bears larger but seedy fruit that are less easy to peel. The average number of segments are fewer than either parent, and fruit are more rounded in shape.

The new cultivar 'RES 19-56' can be compared to the mandarin cultivar 'Marathon' (U.S. Plant Pat. No. 31,347) which is derived from the same parentage as 'RES 19-56'. Trees of 'Marathon' are more vigorous and slower to come into fruiting than 'RES 19-56'. Foliage of 'Marathon' is slightly undulate, in contrast with 'RES 19-56', in which leaf margins are dentated with a split end. Fruit of 'RES 19-56' are smaller in all dimensions and weigh less, and they are much easier to peel cleanly than those of 'Marathon'. Further, the fruit of 'RES 19-56' has fewer segments on average, as well as deeper external and internal color. Fruit of 'Marathon' are firmer and hold longer on the tree than those of 'RES 19-56'.

DESCRIPTION OF THE FIGURES

The accompanying photographs (as shown in FIGS. 1-3) illustrate the overall appearance of the new mandarin cultivar 'RES 19-56'. These photographs show the colors as true as can be reasonably obtained in colored reproductions of this type. Colors in the photographs may differ slightly from the color values cited in the detailed botanical description, which accurately describe the colors of the new mandarin cultivar.

DETAILED BOTANICAL DESCRIPTION OF THE CULTIVAR

Figure 1A:
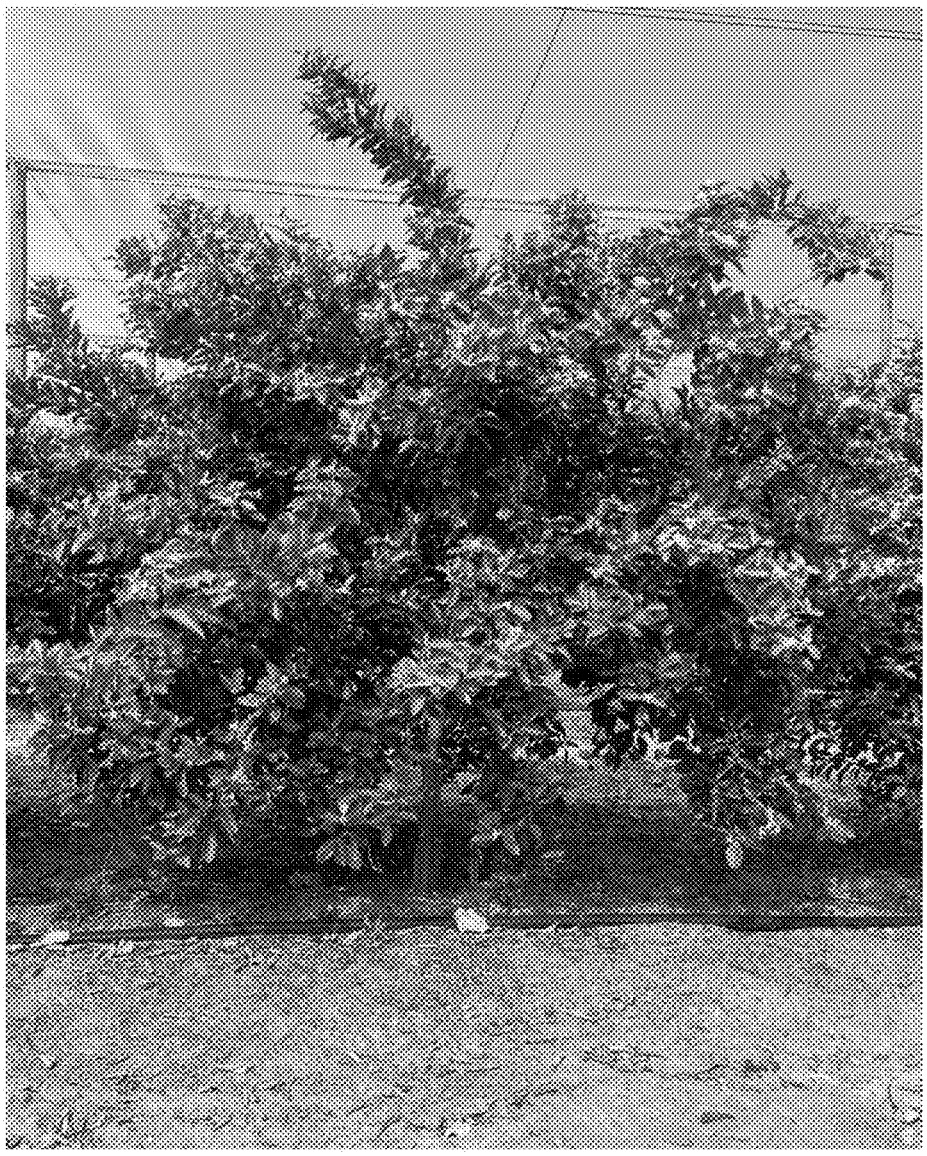
FIG. 1A shows a four-year-old tree of the new mandarin cultivar 'RES 19-56' grown on 'US 897' rootstock in a CUPS structure, showing tree shape and spreading habit.
Figure 1B:
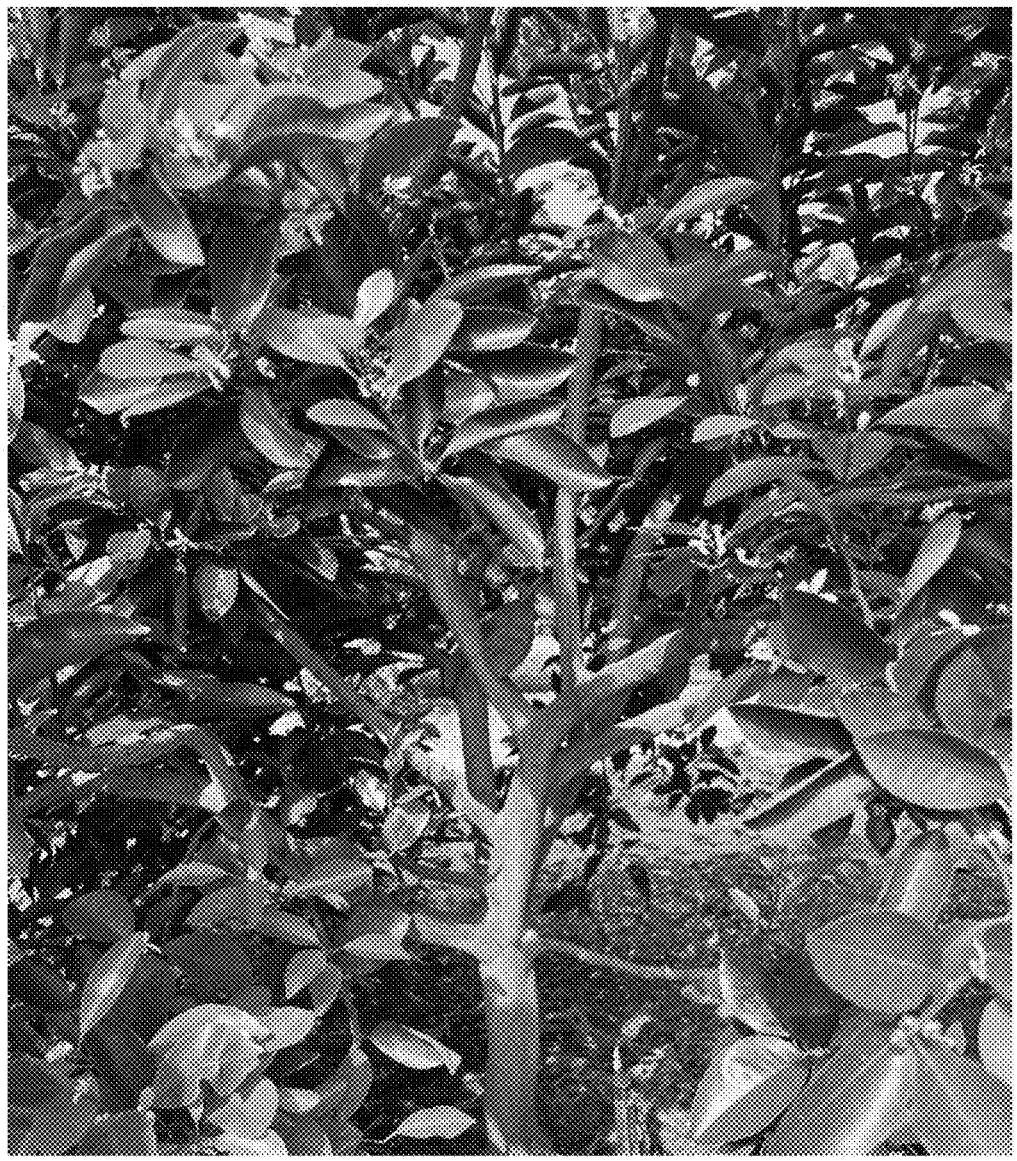
FIG. 1B shows a graft union between the new cultivar 'RES 19-56' and 'US 897' rootstock, as well as internal branching habit, in a CUPS structure.
Figure 1C:
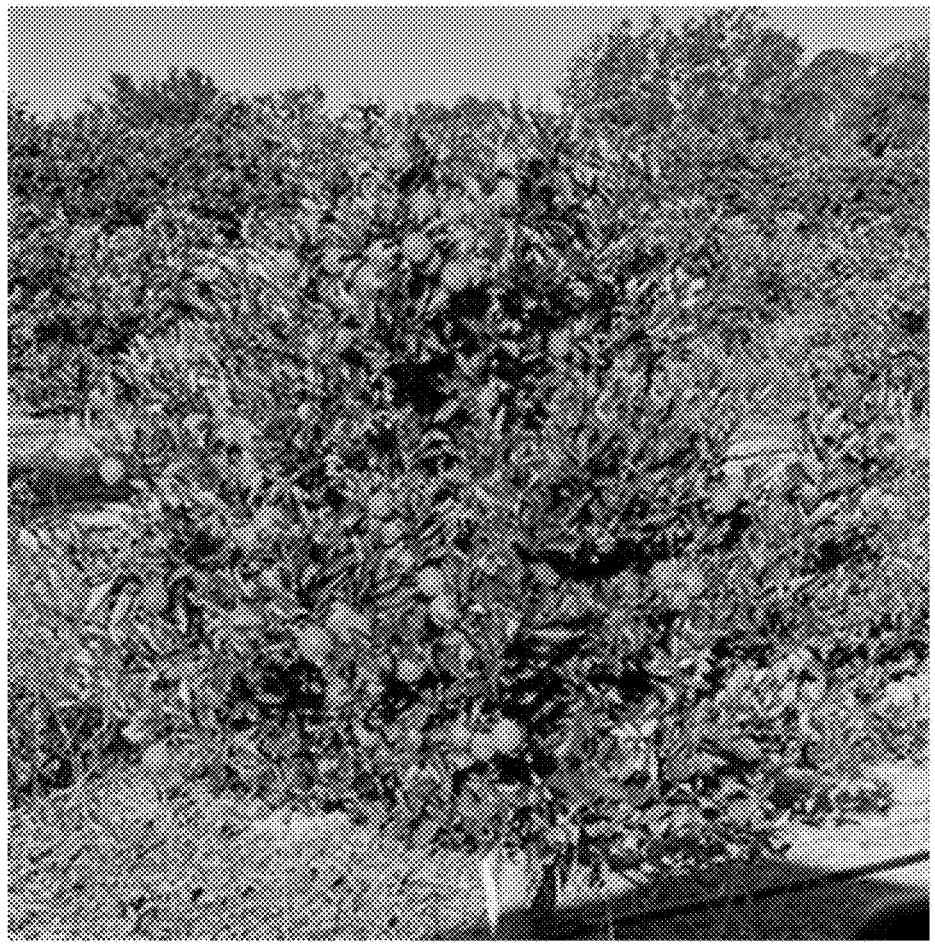
FIG. 1C shows a 2.5-year-old field-grown tree of the new cultivar with mature fruit in early November 2023 in north central Florida.
Figure 2A:
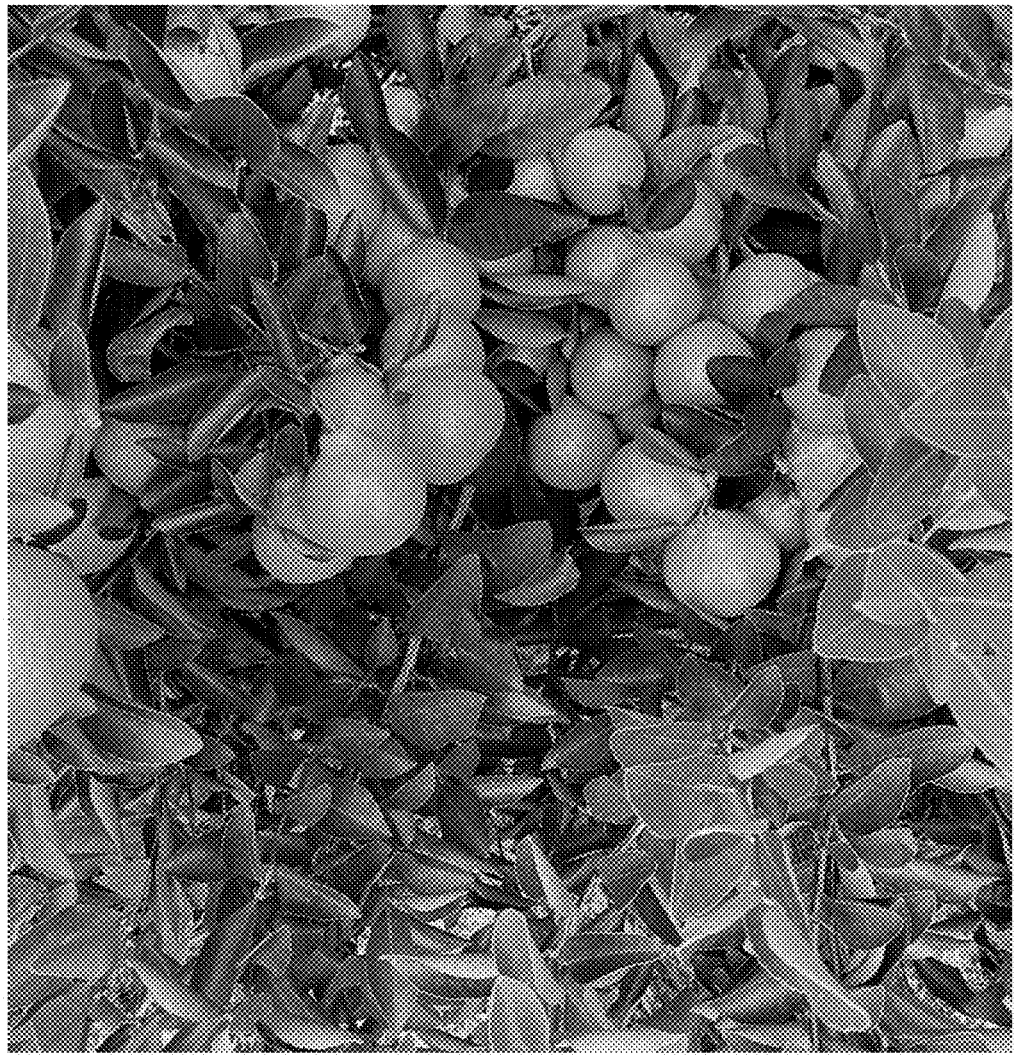
FIG. 2A shows clusters of fruit set on a two-year-old tree of the new cultivar at fruit maturity in a CUPS structure in October 2021 (planted in 2019)
Figure 2B:
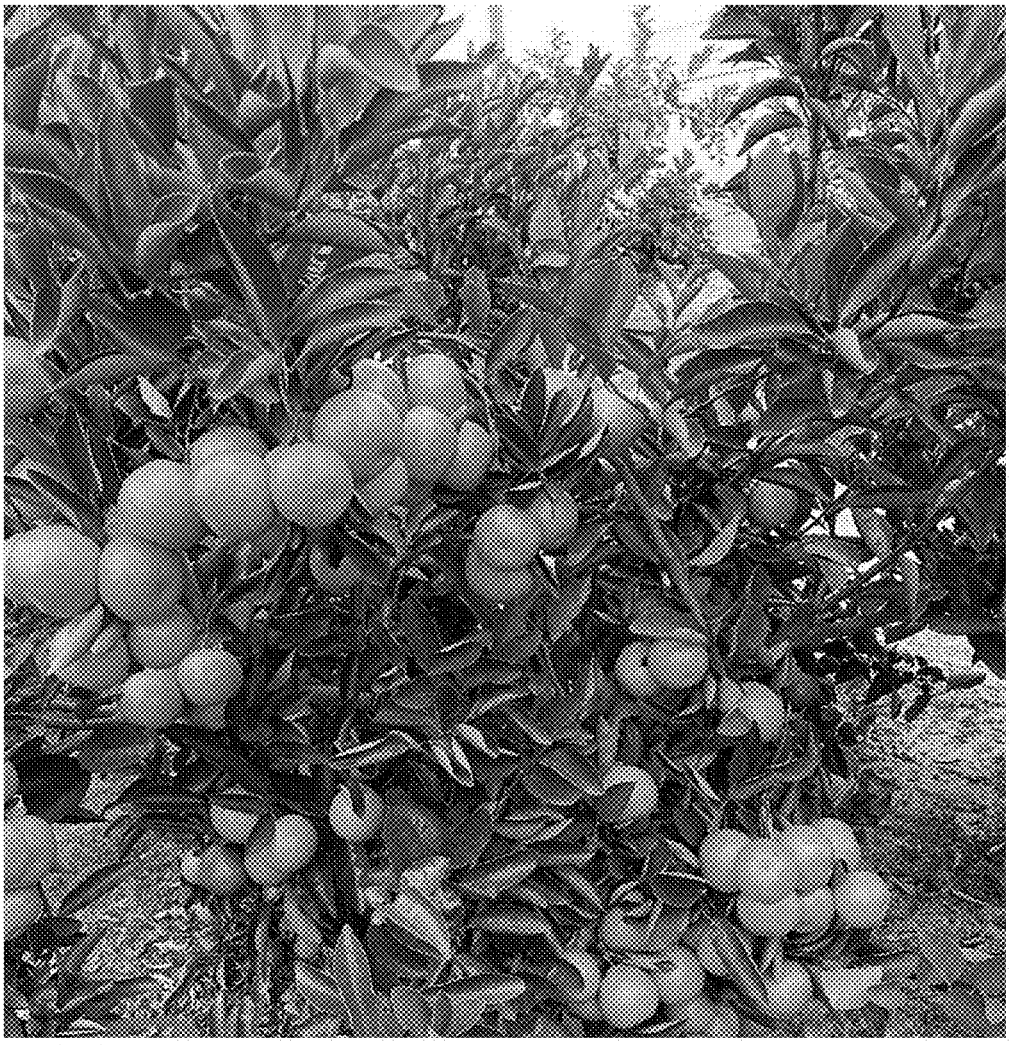
FIG. 2B shows clusters of fruit set on another two-year-old tree of the new cultivar at fruit maturity in a CUPS structure in October 2021 (planted in 2019)
Figure 2C:
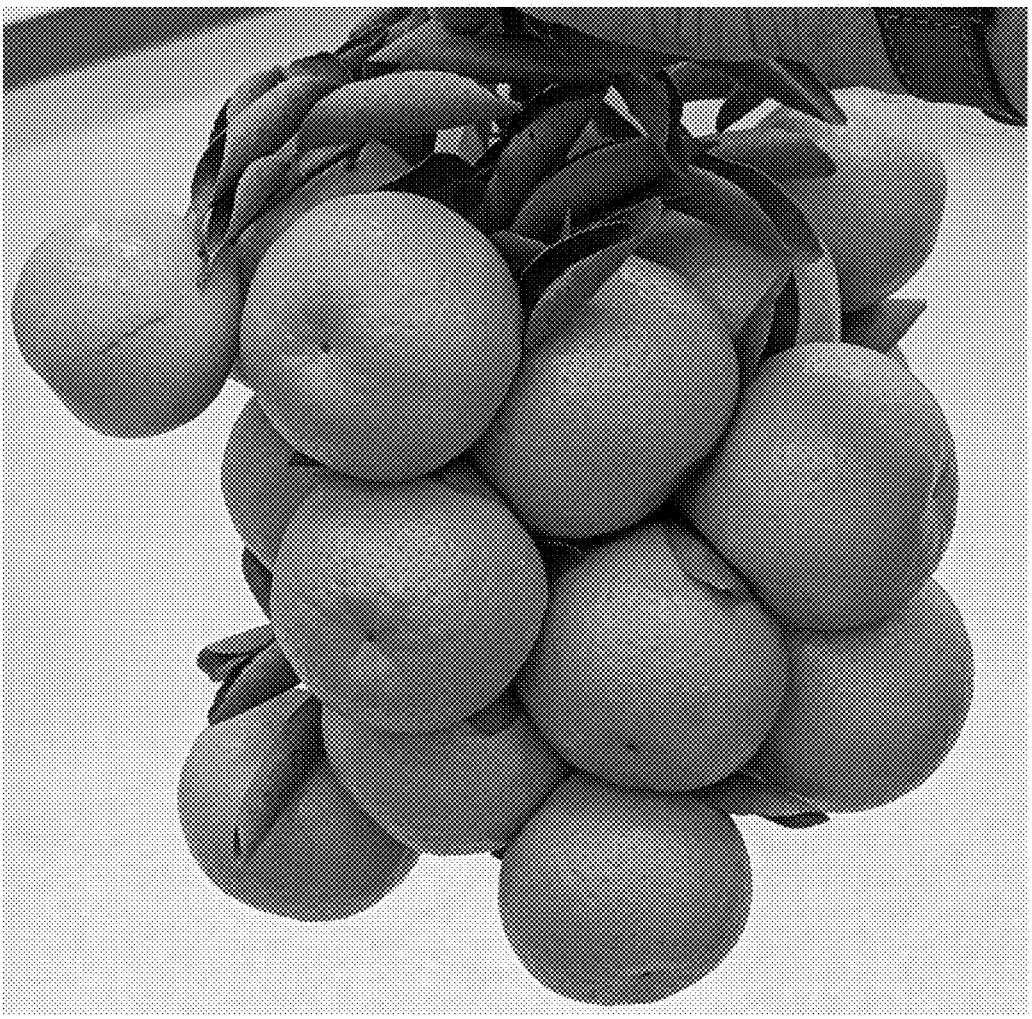
FIG. 2C shows a large cluster of fruit growing on one stem of a 2-year-old tree of the new cultivar in a CUPS structure in October 2021.
Figure 3A:
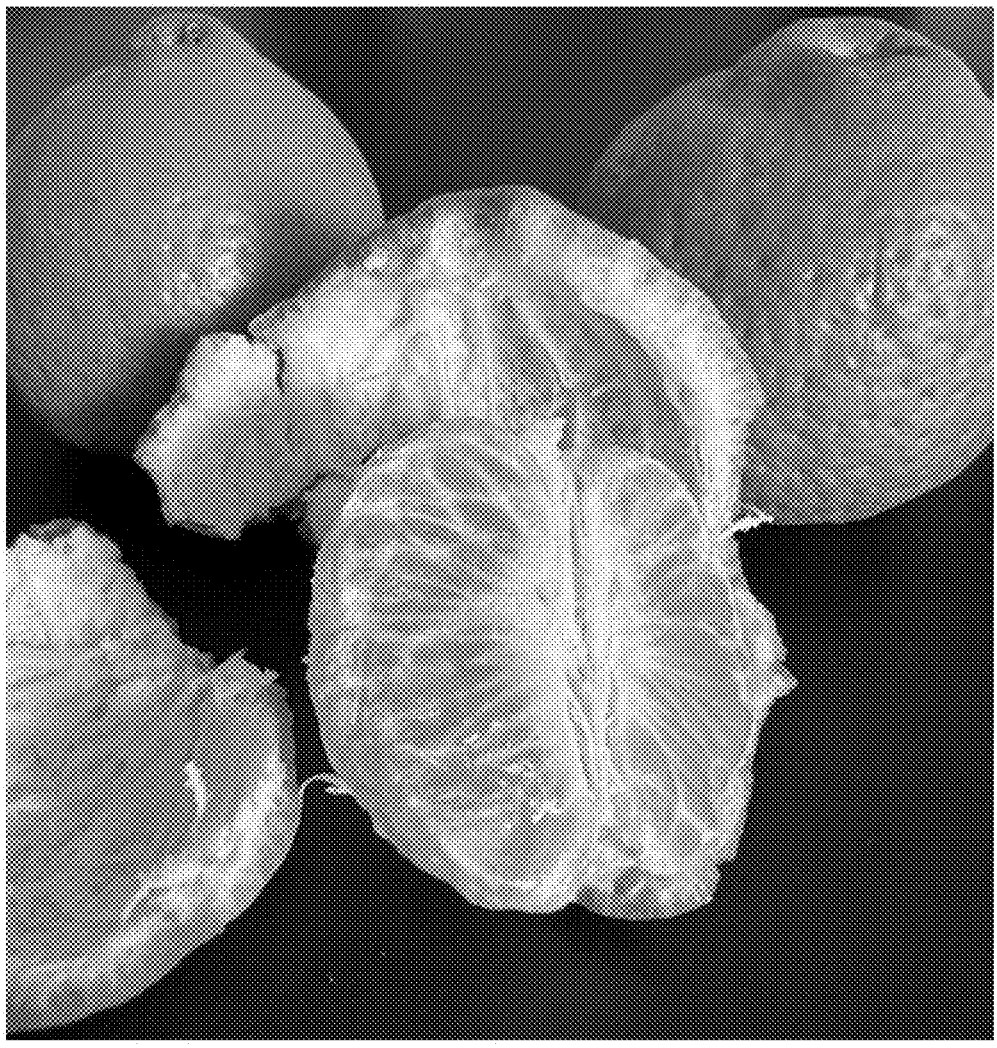
FIG. 3A shows fruit from a field-grown tree of the new cultivar in north central Florida, harvested in early November 2023, with easily removed peel, intact segments, spherical shape, and slight neck at the stem end of the fruit.
Figure 3B:
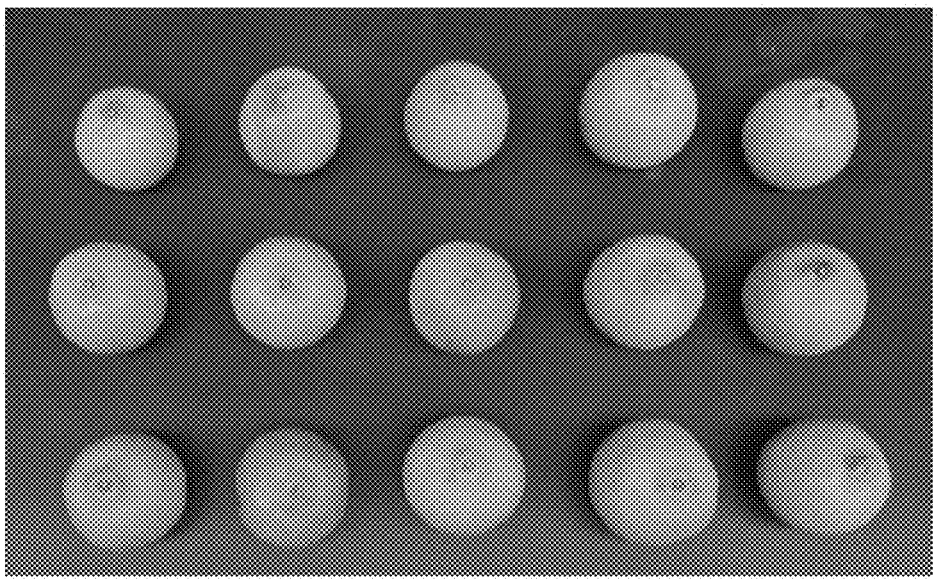
FIG. 3B shows fruit harvested from trees of the new cultivar grown in a CUPS structure.
Figure 3C:
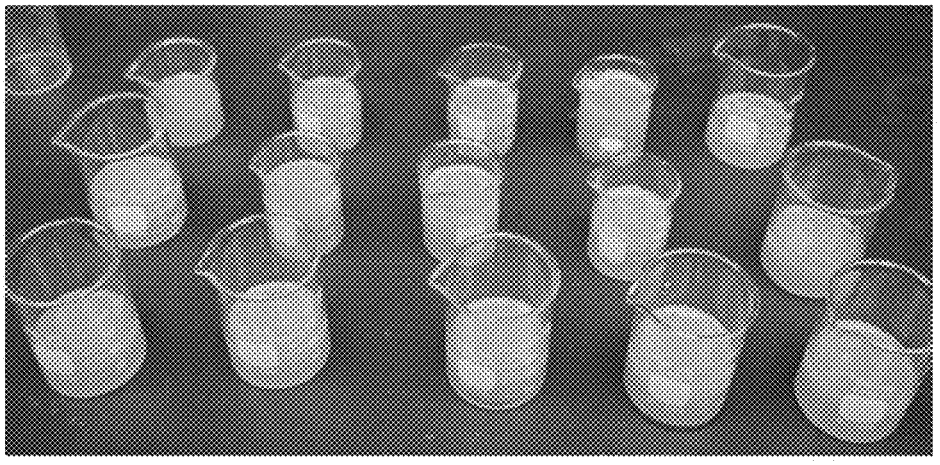
FIG. 3C shows juice samples from the individual fruit shown in FIG. 3B.
Figure 3D:
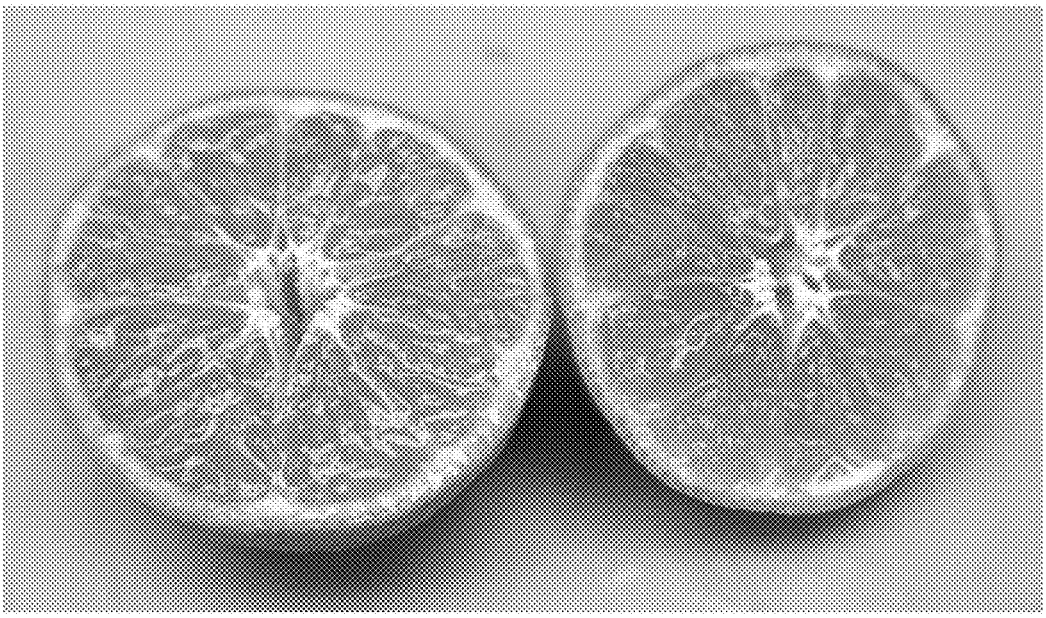
FIG. 3D shows fruit harvested in late October 2023 from trees of the new cultivar grown in a CUPS structure, cut equatorially.
Figure 3E:
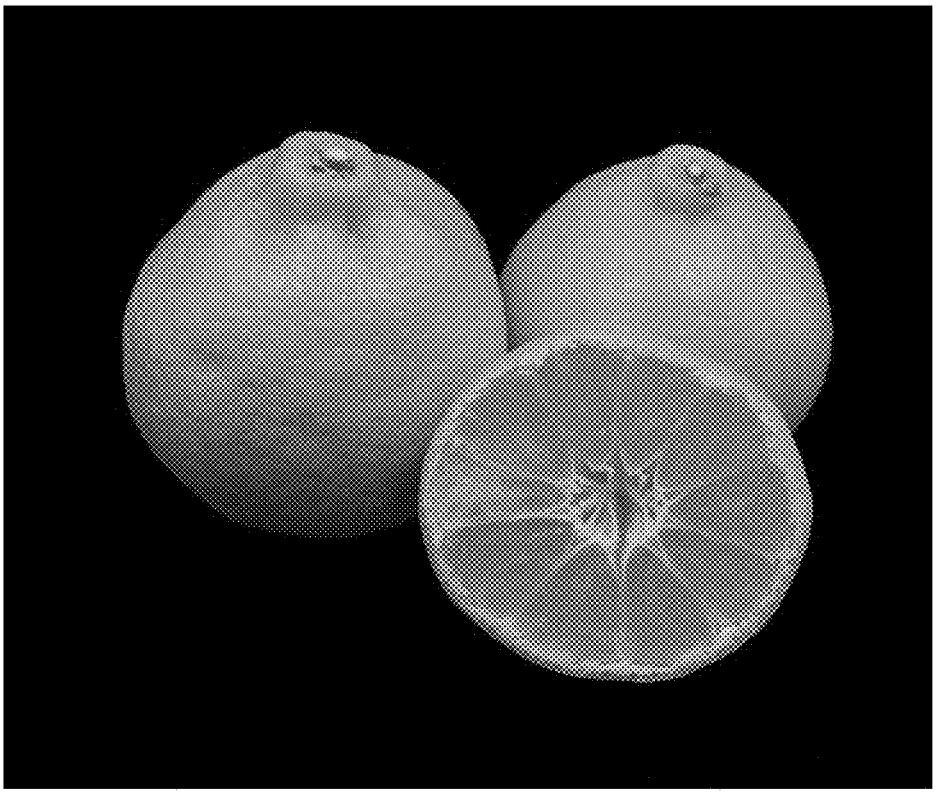
FIG. 3E shows a close-up view of whole and cut mature fruit of the new cultivar, harvested mid-November 2023 from trees grown in a CUPS structure.
Figure 4A:
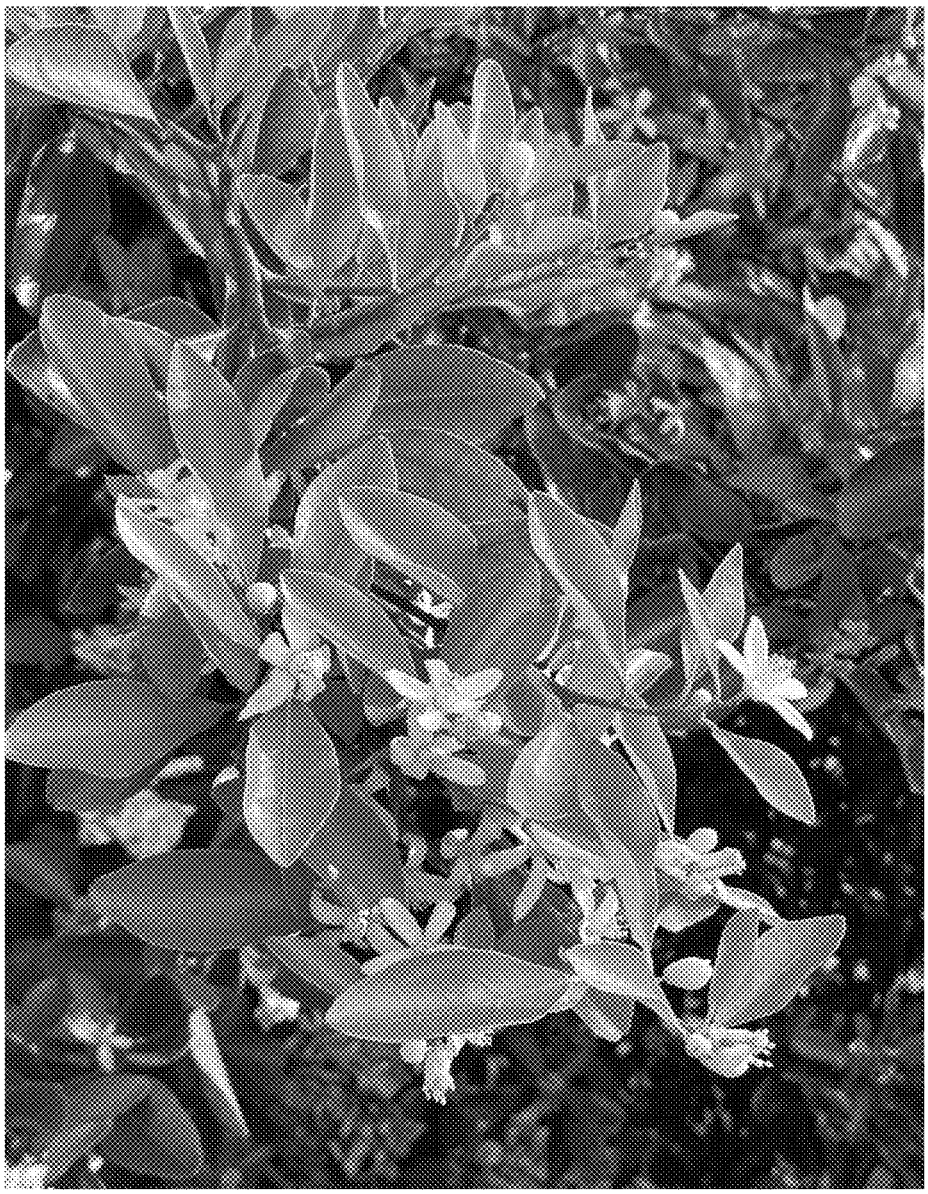
FIG. 4A shows flowering of young flush on a 4-year-old tree of the new cultivar grown in a CUPS structure in Spring 2023.
Figure 4B:
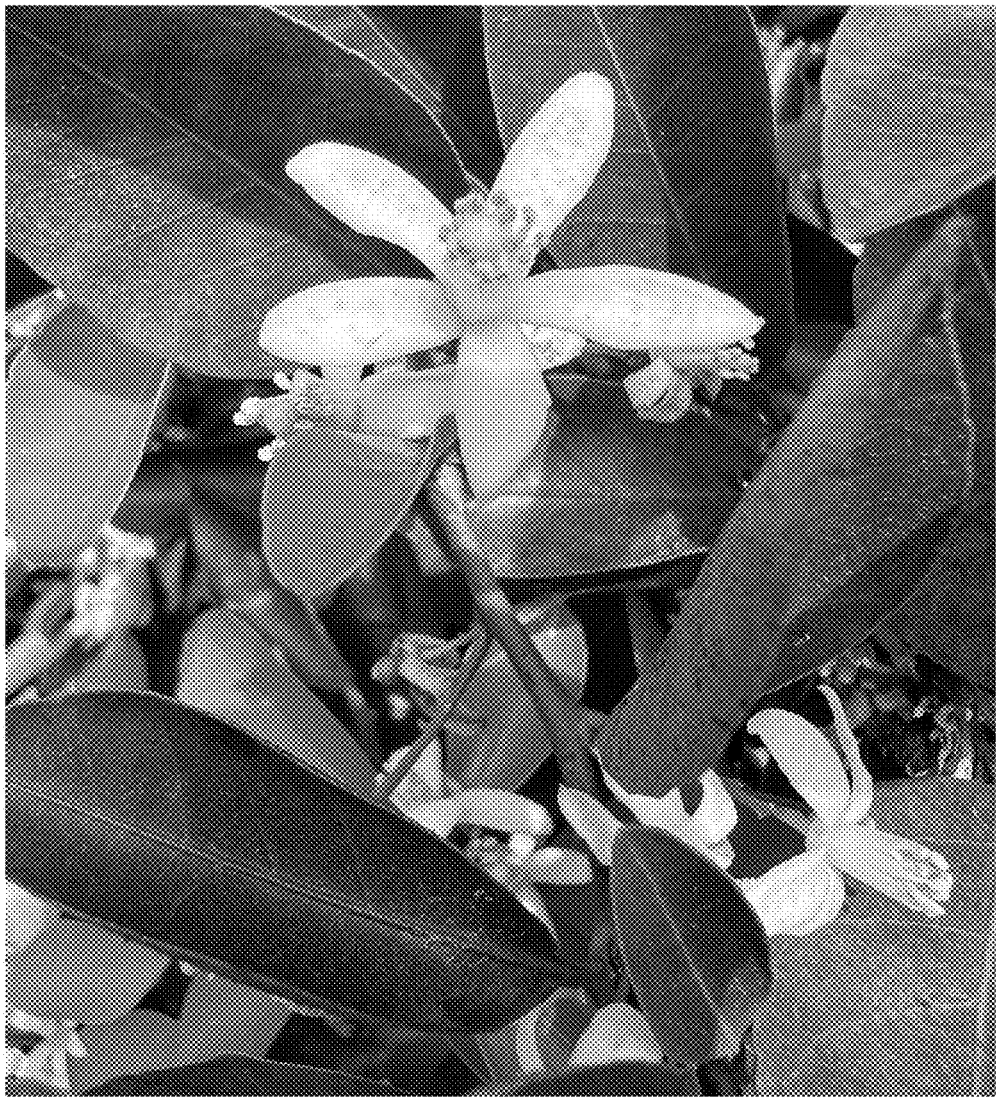
FIG. 4B shows a close-up view of flowers on a 4-year-old tree of the new cultivar grown in a CUPS structure in Spring 2023, showing range from pre-anthesis through post-anthesis, including one small green fruitlet.
Figure 4C:
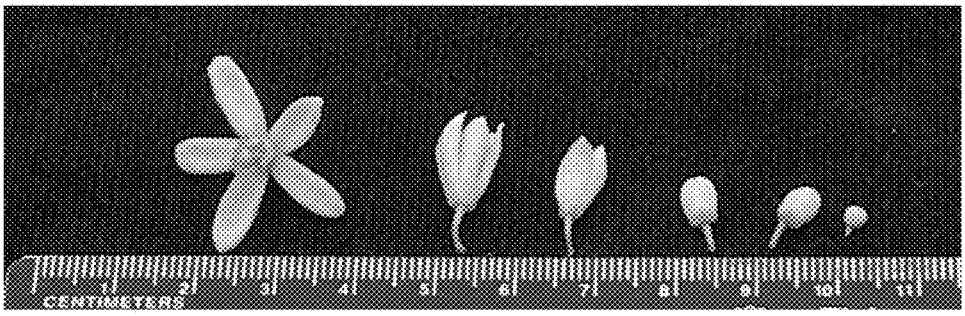
FIG. 4C shows a close-up view of buds and flowers alongside a rule for measurement.
Figure 4D:
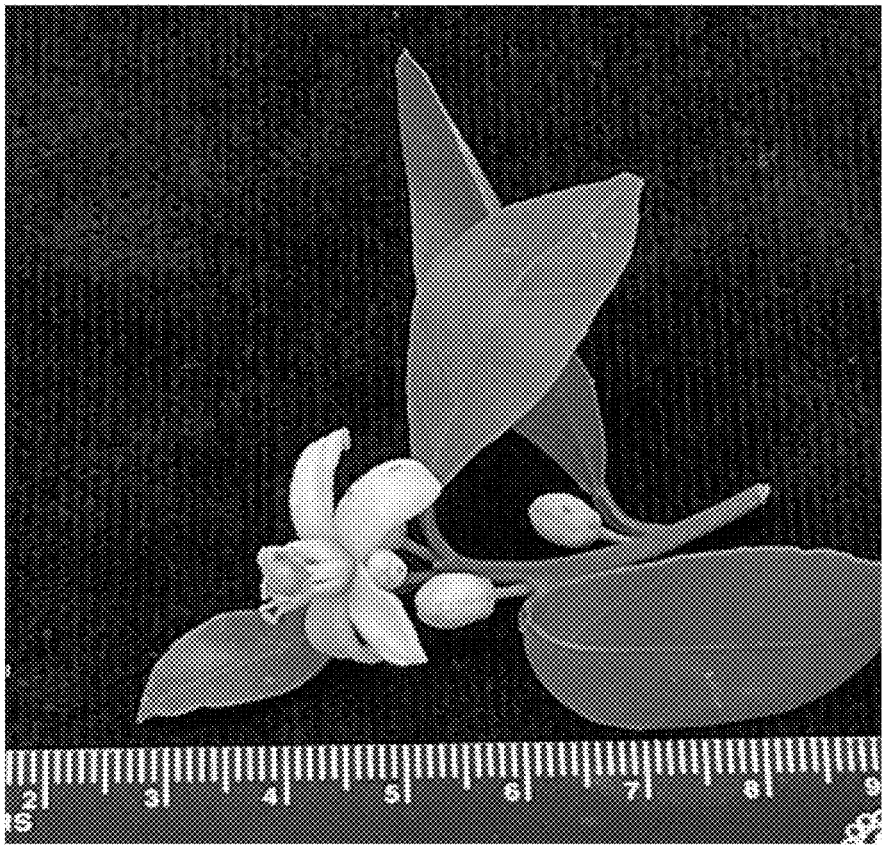
FIG. 4D shows a close-up view of buds and flowers alongside a rule for measurement.
Figure 4E:
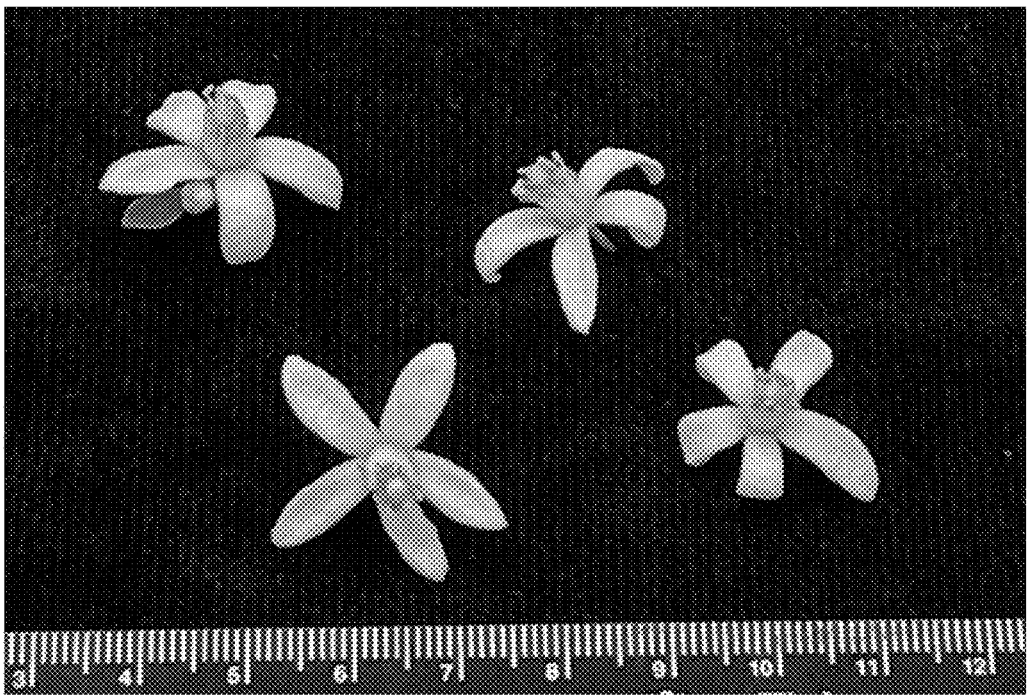
FIG. 4E shows a close-up view of buds and flowers alongside a rule for measurement.
Figure 5A:
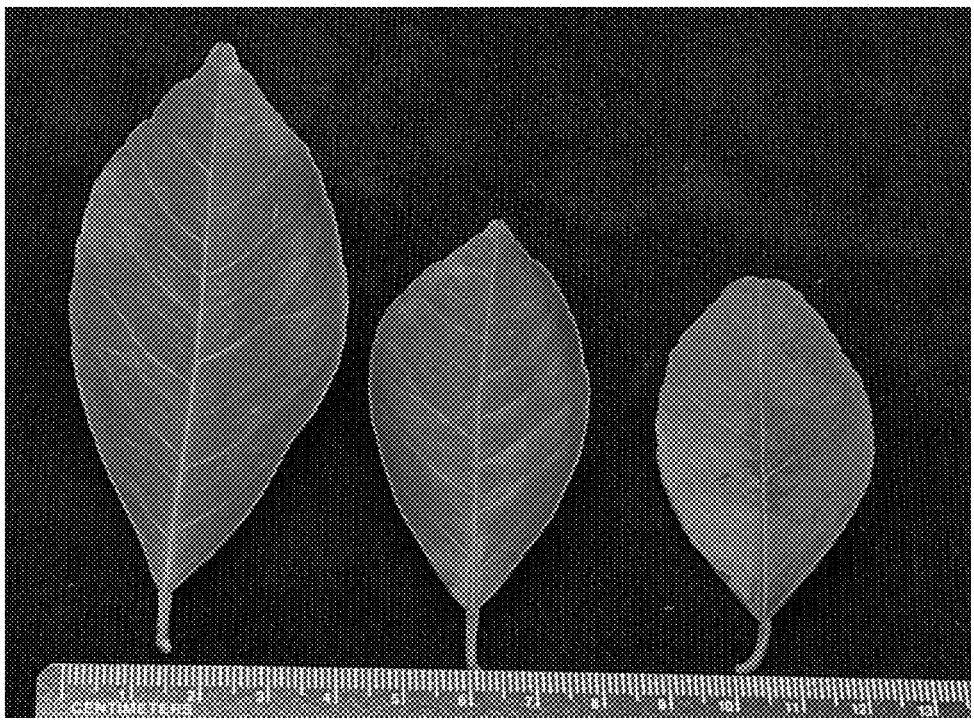
FIG. 5A shows a close-up view of leaves of the new cultivar alongside a ruler for measurement.
Figure 5B:
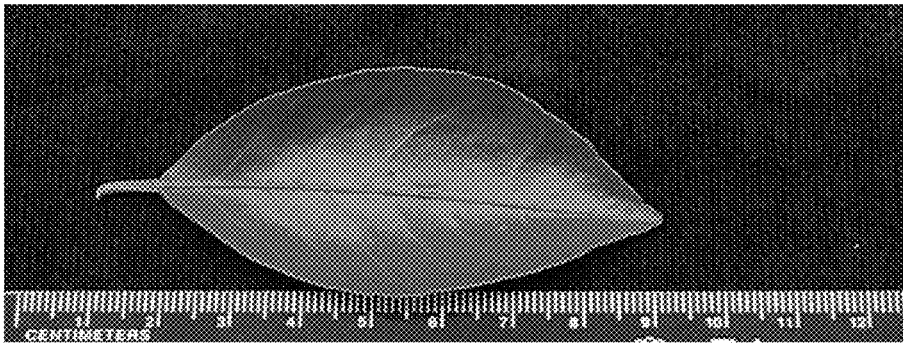
FIG. 5B shows a close-up view of leaves of the new cultivar alongside a ruler for measurement.
Figure 6:
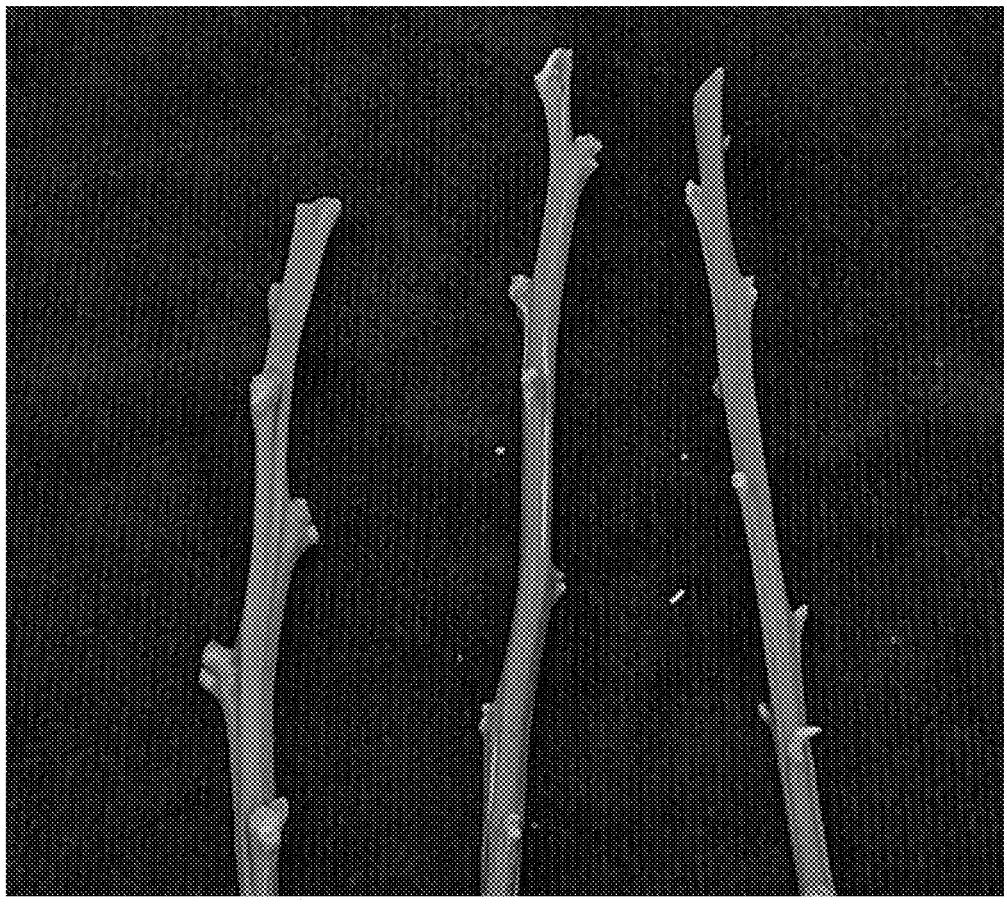
FIG. 6 shows typical bud sticks cut for propagation from the new cultivar.

In the following description, color references are made to The Royal Horticultural Society (R.H.S.) Colour Chart, 1986 Edition, except where general terms of ordinary dictionary significance are used.

Vegetative descriptions are based on 4.5-year-old trees on 'US 897' rootstock (not patented), grown in a covered structure (CUPS) in Central Florida, and free of HLB.

BOTANICAL DESCRIPTION

Botanical classification:

*Family*.—Rutaceae.

*Botanical name*.—*Citrus reticulata* hybrid.

*Common name*.—Mandarin.

*Cultivar*.—'RES 19-56'.

Parentage: 'Daisy' mandarin (seed parent) x 'Mukaku Kishu' (pollen parent, also known as 'Seedless Kishu'), both publicly available and unprotected cultivars.

Tree:

*Ploidy*.—Diploid.

*Size*.—Medium.

*Width across row*.—2.3 meters on average.

*Width down row*.—2.4 meters on average.

*Tree height*.—2.6 meters on average.

*Tree canopy diameter*.—2.7 meters on average.

*Vigor*.—Moderate.

*Density*.—Dense foliage.

*Tree shape* (*form*).—Oblate (obloid) to round, spreading.

*Growth habit* (*current season*).—Spreading growth habit. Vegetative growth in general is moderate.

Trunk:

*Trunk diameter*.—Approximately 6.2 cm at 30 cm above the ground.

*Trunk texture*.—Relatively smooth.

*Trunk bark color*.—RHS N199A.

Branches:

*Branch length*.—2 meters on average.

*Branch diameter*.—3.8 cm on average.

*Crotch angle*.—Acute with a degree of 75-80 on average (less than 90 degrees) in the middle of the tree, with some on the outside being more than 90 degrees (110-115).

*Branch texture*.—Relatively smooth with very small spines.

*Branch color*.—RHS 199B (Grey-Brown Group).

Leaves:

*Size* (*lamina average*).—Length: 111 mm on average. Width: 45 mm on average. L/W ratio: 2.4 on average. Thickness: Regular (average thickness). Type: Simple. Shape: Elliptical. Apex: Acute to retuse. Base: Acute. Margin: Dentated with split end.

*Surface*.—Upper surface: Smooth. Lower surface: Medium veins that are pinnately netted.

*Color*.—Upper surface (adaxial): RHS 137A (Green Group). Lower surface (abaxial): RHS 137D (Green Group).

*Petiole*.—Shape and attachment: Brevipetiolate; shorter than the leaf lamina. The junction between the petiole and the lamina is articulate. Shape (petiole wing): Obovate with a narrow end at the base. Length: 11 mm on average. Width: 1-1.1 mm on average. Color: RHS 137B (Green Group).

Flowers:

*Type*.—Perfect.

*Flowers bearing*.—Single or clusters. Branches have flowers grown in clusters. Each cluster consists of 3-5 flowers. Individual flowers are grown from leafy terminals and leaf axillaries.

*Flower diameter*.—20 mm on average.

*Flower depth*.—17 mm on average.

*Flower blooming period*.—February to March, depending on season.

*First bloom*.—Earliest is generally the 1$^{st}$ of February.

*Full bloom*.—Late February to early March, depending on season.

*Fragrance*.—Fragrant. Strongly aromatic, typical *Citrus* blossom fragrance.

*Flower buds' size*.—Length: 1.5 mm on average for the initial visible flower bud; 2.3 mm on average for the mature flower buds before opened. Diameter: 1.2 mm on average in the initial visible flower bud; 5.2 mm on average in the mature bud.

*Flower bud shape*.—Initial visible flower bud with round dome shape; mature flower bud with elongated olive shape.

*Flower bud color*.—RHS 144C (yellow-green) for the initial visible flower bud; RHS NN 155B (white) for mature buds.

Reproductive organs:

*Fertility*.—Pollen fertile, female sterile. Completely seedless by virtue of arrested embryo development, which is typical of 'Mukaku Kishu' F1 hybrids.

*Petals*.—Number: 5. Petal length: 14 mm on average. Petal width: 4.7 mm on average. Petal shape: Flat spatula shape. Apex shape: Smooth with obtuse angle. Base shape: Obtuse. Petal Color: Upper Surface: RHS NN 155C (White Group). Lower surface: RHS NN 155B (White Group). Margin: Smooth. Sepal: Number (per flower): 5. Shape: Delta shaped with an acute angle at apex, although some with flat angle. Length: 3.5 mm on average. Width: 2 mm on average. Apex shape: Acute angle at apex. Margin: Smooth. Color: Upper surface: RHS 158A (Green-White Group). Lower surface: RHS 157A (Green-White Group).

*Pedicel*.—Length: 8 mm on average. Diameter: 1.5 mm on average. Color: RHS 144A (Yellow-Green Group).

*Stamen*.—Number: 23 per flower on average. Length: 14 mm on average.

*Anther*.—Length: 2 mm on average. Width: 0.7 mm on average. Color: RHS 14B (Yellow Orange Group). Amount of pollen: Moderate. Pollen color (general): RHS 13A (Yellow Group).

*Pistil*.—Number: 1. Length: 14 mm on average. Color: RHS 153B (Yellow Green Group). Style length: 12 mm on average. Style diameter: 1.4 mm on average. Style color: RHS 144A (Yellow Green Group). Ovary shape: Oval shape. Ovary diameter: 4 mm on average. Ovary color: RHS 145C (Yellow Green Group).

Fruit:

*Size*.—Small.

*Average weight* (*per individual fruit*).—62.7 g on average.

*Length* (*height*).—6.5 cm on average.

*Diameter*.—6.35 cm on average.

*Shape*.—Spherical.

*Shape* (*cross-section*).—Round.

*Glossiness of fruit surface*.—Medium glossiness.

*Apex*.—Round with a small or slight neck at the stem end of the fruit.

*Base*.—Round.

*Areola*.—Absent.

*Navel*.—Absent.

*Time of maturity*.—Fruit can be consumed generally between mid-September to mid-December.

*Harvest*.—Date of first pick: 15 September. Date of last pick: 15 November.

*Fruit stem*.—Length: 10 mm on average. Diameter: 2 mm on average.

*Color*.—RHS 189A (Greyed-green Group).

Rind:

*Adherence*.—Easy to peel. Amount of albedo adhering to the flesh is very small to absent.

*Thickness*.—Thin (1.2 mm on average).

*Texture*.—Medium firm.

*Surface texture*.—Medium smooth.

*Color*.—Flavedo (epicarp): RHS N25B (Orange Group). Albedo (mesocarp): RHS N19D (Yellow-Orange Group).

*Style end*.—Closed.

*Rind oil cell density*.—70-100 cell/square cm.

*Oil gland size*.—0.5 mm on average.

Flesh:

*Number of segments*.—10 on average.

*Segment length*.—Not available.

*Segment width*.—1.5 cm.

*Juice*.—Abundant.

*Color*.—RHS 23B Yellow-Orange Group.

*Texture*.—Soft to medium.

*Vesicle thickness*.—Thin, tender.

*Length*.—5 mm on average.

*Diameter*.—2 mm on average.

*Juice quality* (*from early harvest on* 15 *Sep.* 2021).—Brix: 9.9.Acidity (average): 0.6%. Juice color: Not determined. Lb solid/box: Not determined, fresh market variety, not intended for juice processing.

*Juice quality* (*from mid-season harvest on* 24 *Oct.* 2022).—Brix: 10.4. Acidity (average): 0.43%. Ratio: Approximately 24. Juice color: RHS 23B (Yellow-Orange Group). Lb solid/box: Not determined, fresh market variety, not intended for juice processing.

Seeds:

*Presence*.—Completely seedless, no seeds ever observed.

*Fruit parthenocarpy*.—Yes, fruit set in protected structure in the absence of pollinating insects and without limb girdling or applications of gibberellic acid to support fruit set.

Resistance to disease: No systematic disease resistance testing conducted. No obvious disease problems noted, very clean fruit produced with minimal chemical treatments to control diseases.

What is claimed is:

1. A new and distinct mandarin plant named 'RES 19-56' as illustrated and described herein.

* * * * *